United States Patent [19]

Thuillier et al.

[11] 4,029,808

[45] June 14, 1977

[54] THIENYL PHENYL O-(AMINOALKYL)-KETONE OXIME AND FURYL PHENYL O-(AMINOALKYL)-KETONE OXIME CORONARY VASODILATORS

[75] Inventors: Germaine Thuillier, Paris; Jacqueline Laforest, Vincennes; Pierre Bessin, Chilly-Mazarin, all of France

[73] Assignee: C.E.R.P.H.A. a French Society organised under the laws of France, Arcueil, France

[22] Filed: Oct. 15, 1974

[21] Appl. No.: 515,063

[30] Foreign Application Priority Data

Oct. 19, 1973 France .............................. 73.37444

[52] U.S. Cl. .......................... 424/275; 260/240 G; 260/329 AM; 260/347.7; 424/285
[51] Int. Cl.² ................. A61K 31/34; A61K 31/38

[58] Field of Search ........................... 424/285, 275; 260/347.7, 240 G, 329 AM

[56] References Cited

UNITED STATES PATENTS

| 3,084,171 | 4/1963 | Von Esch et al. .............. 260/347.7 |
| 3,272,833 | 9/1966 | Von Esch et al. .............. 260/295.5 |
| 3,895,039 | 7/1975 | Perrqnnet et al. .............. 260/347.7 |

*Primary Examiner*—Leonard Schenkman

[57] ABSTRACT

The invention relates to novel thienyl phenyl O-(aminoalkyl)-ketone oximes and to novel furyl phenyl O-(aminoalkyl)-ketone oximes.

These novel compounds exhibit a coronary vasodilatatory activity and may be used in the treatment of cardiopathies.

The invention also relates to a process for preparing these novel compounds by reaction of a diaromatic ketone with a hydroxylamine.

11 Claims, No Drawings

THIENYL PHENYL O-(AMINOALKYL)-KETONE OXIME AND FURYL PHENYL O-(AMINOALKYL)-KETONE OXIME CORONARY VASODILATORS

This invention relates to diaromatic O-(aminoalkyl)-oximes. The invention also relates to the preparation of diaromatic O-(aminoalkyl)-oximes and to pharmaceutical compositions comprising these oximes as active ingredient.

Accordingly, the invention provides novel diaromatic O-(aminoalkyl)-oximes having the following general formula (I):

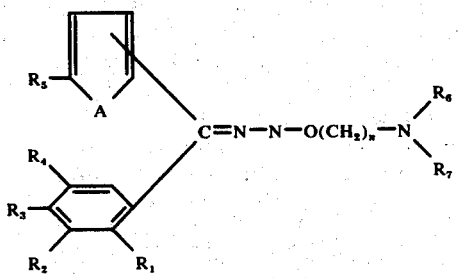

in which A represents O or S; $R_1$, $R_2$, $R_3$ and $R_4$, which may be identical or different, represent the hydrogen atom, a halogen atom, a lower alkyl group, a lower alkoxy group or a lower alkoxylidene group; $R_5$ represents the hydrogen atom, a halogen atom, a lower alkyl group or the nitro group; n is a small integer; $R_6$ and $R_7$, which may be identical or different, represent a lower alkyl group or $R_6$ and $R_7$ may together with the nitrogen atom to which they are attached form a 5- to 7-membered N-heterocyclic group which may contain a second hetero atom and acid addition salts of the amino group.

The compounds of formula I and the acid addition salts thereof according to the present invention include:

a. the geometric isomer such that the oxime has the trans configuration in relation to the heterocyclic group;

b. the geometric isomer such that the oxime has the cis configuration in relation to the heterocyclic group; and c. mixtures of the two geometric isomers of one and the same compound of formula I.

The second hetero atom in the 5 to 7-membered heterocyclic group may be, for example, O, N or S.

By lower alkyl groups, lower alkoxy groups and lower alkoxylidene groups are meant in this context groups containing at the most four carbon atoms. By halogen atoms are meant fluorine, chlorine bromine and iodine and n is an integer less than 5, preferably 2 or 3.

These novel chemical compounds have very important pharmacological properties. They have been shown to have a coronary vasodilatory activity, to slow down the heart rate and to reduce the diastolic pressure and to protect animals against digitaline poisoning. These products, which have a completely original therapeutic action, may so be used beneficially in the treatment of cardiopathies. The invention also proposes a therapeutic composition which can be administered orally or parenterally and which contains, as active ingredient, at least one of the geometric isomers of the oxime ethers of formula I or one of their pharmaceutically acceptable acid addition salts in combination with an excipient therefor. The unit dose for oral administration is 1 to 100 mg and for parenteral administration 1 to 50 mg. The number of daily doses varies according to the nature of the case under treatment.

The invention also provides a process for the preparation of compounds of formula I wherein a diaromatic ketone of the formula (II)

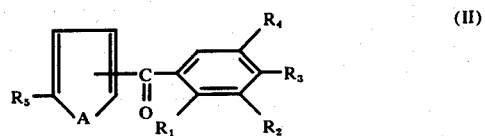

wherein A, $R_1$, $R_2$, $R_3$, $R_4$ and $R_5$ are as defined for formula I is reacted with a hydroxylamine of the formula $H_2N$-O-R wherein R is the hydrogen atom or the group $(CH_2)_n$—$NR_6R_7$ wherein n, $R_6$ and $R_7$ are as defined for formula I; and when R is $(CH_2)_n$—$NR_6R_7$; the reaction is carried out in an alcoholic or aqueous alcoholic solvent in an acidic medium and when R is H the reaction is carried out in pyridine under reflux and the intermediate compound thereby obtained is reacted in the presence of a base with a compound of the formula X-$(CH_2)_n$—$NR_8R_9$ wherein X is a halogen atom and $R_8$ and $R_9$ represent $R_6$ and $R_7$ or the hydrogen atom, n, $R_6$ and $R_7$ being as just defined, and when $R_8$ and $R_9$ represent H the intermediate compound obtained is reacted with a halogenated alkane. A mixture of the two geometric isomers of the oximes is obtained in all cases.

The acid addition salts of the amino group are prepared by the action of a mineral or organic acid on the compounds thus obtained. The acid used may be, in particular, a hydrohalic acid, fumaric acid, maleic acid, methanesulphonic acid or glycollic acid.

The two geometric isomers of these oxime ethers are difficult to separate when the amine function has not been salified. The differences in solubility of the acid addition salts enables separation to be achieved by successive recrystallisations.

The ketones of formula II, some of which, to the knowledge of the Applicant, have not hitherto been described, may be prepared in particular by Friedel-Crafts reactions, either by the action of an $R_5$-substituted heterocyclic acid chloride on a benzene derivative containing the substituents $R_1$, $R_2$, $R_3$ and $R_4$ in solution in methylene chloride and in the presence of anhydrous aluminum chloride or by the action of an $R_1$-, $R_2$-, $R_3$- and $R_4$-substituted benzoic acid chloride on an $R_5$-substituted heterocyclic compound in solution in benzene and in the presence of anhydrous stannic chloride. The O-(dialkylaminoalkyl)-hydroxylamines are obtained in the form of dihydrochlorides, for example by hydrolysis of the appropriate O-(aminoalkyl)-acetone oxime according to the method described by "WINTERNITZ and LACHAZETTE (Bull. Soc. Chim. 664-9 (1958))".

Further advantages and characteristics of the invention will be better understood with the aid of the examples of preparation given below which are in no way limiting but given by way of illustration. The melting points mentioned in the examples were determined on a Kofler bench. All the compounds described were the object of thorough analytical and structural investigation. The results of the elementary analyses obtained conform to the usual standards (determination of the percentages of C, H, N and halogens). The appearance of the infra-red and nuclear magnetic resonance spectra confirms the structure of the compounds.

All the O-(aminoalkyl)-oximes of the following examples are oils whereas the acid addition salts of the amine function of these compounds are crystalline solids. Where the two geometric isomers of these oximes were not separated, their relative proportions in the mixtures were determined by studying their nuclear magnetic resonance spectra.

EXAMPLE 1

(2-Chloro)phenyl 2-thienyl-0-(diethylaminoethyl)-ketone oxime

A solution of 11 g of (2-chloro)phenyl 2-thienyl-ketone and 11 g of O-(diethylaminoethyl)-hydroxylamine dihydrochloride (m.p. = 126° C after recrystallisation from ethanol) in 100 ml of absolute ethanol was kept at the reflux temperature of the solvent for 4 hours. Addition of the O-substituted hydroxylamine may also be carried out in several portions. The solvent was removed under reduced pressure. 150 ml of water were poured over the residue and the unreacted ketone was extracted with benzene. The aqueous phase was neutralised by the addition of sodium carbonate before the amine end product was extracted from it with ethyl ether. After washing the ethereal phase with water and drying over sodium sulphate and then magnesium, the solvent was evaporated off under reduced pressure. 12 g of a mixture of the two geometric isomers of (2-chloro)-phenyl 2-thienyl O-(diethylaminoethyl)-ketone oxime were obtained.

The hydrochloride of the amino group was prepared as in the following examples by the addition of anhydrous hydrochloric acid to the solution of the product previously obtained in ethyl ether.

The melting point of the mixture of amine hydrochlorides composed of 65% of the geometric isomer of the oxime in the cis configuration in relation to thiophene and 35% of the trans isomer melted at 164° C The mixture of 25% of the cis isomer and 75% of the trans isomer melts at 138° C.

EXAMPLE 2

(2,4-Dichloro)-phenyl 2-thienyl O-(diethylaminoethyl)-ketone oxime

Applying the method described in Example 1, a mixture of the two isomers of the desired product was obtained in 50% yield from (2,4-dichloro)-phenyl 2-thienyl ketone (m.p. = 75° C after recrystallisation from a mixture of ethanol and water (50:50). The mixture of hydrochlorides composed of 5% of the cis isomer in relation to thiophene and 95% of the trans isomer melts at 163° C.

EXAMPLE 3

(3,4-Dimethoxy)-phenyl 2-thienyl O-(diethylaminoethyl)-ketone oxime 10.25 g of O-(diethylaminoethyl)-hydroxylamine dihydrochloride and a few crops of concentrated hydrochloric acid were added to a solution of 12.4 g of (3,4-dimethoxy)-phenyl 2-thienyl ketone (m.p.=73° C after recrystallisation from isopropyloxide) in 100 ml of ethanol at 95% and the reaction mixture was heated to the reflux temperature of the solvent for 6 hours. The solvent was then evaporated off under reduced pressure. 150 ml of water were poured over the residue and the remaining unreacted ketone used as starting material was extracted with ether. The aqueous phase was neutralised by the addition of sodium carbonate and the end product was extracted with benzene. This oxime ether distilled at 180° C under 0.03 mm Hg. The mixture of hydrochlorides composed of 40% of the transisomer in relation to thiophene and 60% of the cis isomer melts at 128° C.

EXAMPLE 4

(3,4,5-Trimethoxy)-phenyl 2-thienyl O-(diethylaminoethyl)-ketone oxime

Applying the method described in Example 1, 15 g of a mixture of the two geometric isomers of the product were obtained from 11.1 g of (3,4,5-trimethoxy)-phenyl 2-thienyl ketone (m.p. = 83° C after recrystallisation from isopropanol) and 9 g of O-(diethylaminoethyl)-hydroxylamine dihydrochloride.

The amine hydrochloride of the geometric isomer of the oxime ether which had the trans configuration in relation to thiophene melts at 183° C.

EXAMPLE 5

(2,3-Dichloro-4-allyloxy)-phenyl 2-thienyl O-(diethylaminoethyl)-ketone oxime

A solution of 15.6 g of (2,3-dichloro-4-allyloxy)-phenyl 2-thienyl ketone (m.p. = 71° C after recrystallisation from cyclohexane), 10.2 g of O-(diethylaminoethyl)-hydroxylamine dihydrochloride and 10 g of pyridine in 160 ml of absolute ethanol was kept at the reflux temperature of the solvent for 5 hours. The volatile products were evaporated under reduced pressure. The residue was suspended in a normal aqueous hydrochloric acid solution, the ketone used as starting material was extracted with ether and, after neutralisation of the aqueous phase by the addition of potassium carbonate, the desired product was extracted with ether. The ether was evaporated off and, to eliminate pyridine, the residue was taken up with toluene and then evaporated under reduced pressure. A mixture of the two geometric isomers of the desired oxime was obtained in 50% yield.

The amine hydrochloride of the oxime isomer which has the cis configuration in relation to thiophene melts at 156° C after recrystallisation from isopropanol.

EXAMPLE 6

(2,3-Dichloro-4-methoxy)-phenyl 2-thienyl O-(diethylaminoethyl) ketone oxime

Applying the method described in Example 3, 17 g of a mixture of the two geometric isomers of (2,3-dichloro-4-methoxy)-phenyl 2-thienyl O-(diethylaminoethyl)-ketone oxime were obtained from 20 g of (2,3-dichloro-4-methoxy)-phenyl 2-thienyl ketone (m.p. = 112° C after recrystallisation from isopropanol). Applying the method described in Example 1, substantially the same quantity of oxime ether was obtained from 20 g of the ketone dissolved in 250 ml of ethanol.

The mixture of amine hydrochlorides composed of 60% of the geometric isomer of the oxime which has the trans configuration in relation to thiophene and 40% of the cis isomer melts at 158° C.

The hydrochloride of the pure cis isomer obtained after several recrystallisations of the aforesaid mixture from ethanol melts at 184° C.

EXAMPLE 7

(2,3-Dichloro-4-methoxy)-phenyl 2-thienyl O-(dimethylaminoethyl)-ketone oxime 4.5 g of this compound were obtained by the method described in Example 1 from 10 g of (2,3-dichloro-4-metoxy)-phenyl 2-thienyl ketone and 6.1 g of O-(dimethylaminoethyl)-hydroxylamine hydrochloride (m.p. = 194° C).

The amine hydrochloride of the geometric isomer which has the cis configuration in relation to thiophene melts at 160° C whereas the mixture of hydrochlorides consisting of 90% of the isomer which has the trans configuration in relation to thiophene and 10% of the cis isomer melts at 248° C.

EXAMPLE 8

(2,3-Dichloro-4-methoxy)-phenyl 2-thienyl O-(dimethylaminopropyl)-ketone oxime

Applying the method described in Example 1, 3 g of the oxime ether were obtained from 10 g of (2,3-dichloro-4-methoxy)-phenyl 2-thienyl ketone and 6.5 g of O-(dimethylaminopropyl)-hydroxylamine dihydrochloride (m.p. = 167° C after recrystallisation from ethanol).

The mixture of hydrochlorides containing 90% of the isomer of the cis configuration in relation to thiophene melts at 199° C whereas the mixture containing 80% of the trans isomer and 20% of the cis isomer melts at 179° C.

EXAMPLE 9

(2,3-Dichloro-4-methoxy)-phenyl 2-thienyl O-(morpholinoethyl)-ketone oxime

Applying the method described in Example 1, 4 g of the mixture of the two isomers of the oxime ether were obtained from 10 g of (2,3-dichloro-4-methoxy)-phenyl 2-thienyl ketone and 7.5 g of O-(-morpholinoethyl)-hydroxylamine dihydrochloride (m.p. = 190° C after recrystallisation from ethanol at 95%). The amine hydrochloride of the isomer which has the cis configuration in relation to thiophene melts at 237° C after recrystallisation from ethanol.

EXAMPLE 10

(2,3-Dichloro-4-methoxy)-phenyl (5-chloro)2-thienyl O-(diethylaminoethyl)-ketone oxime Applying the method described in Example 1 but using butanol-1 as the solvent, the desired oxime is obtained in 75% yield from (2,3-dichloro-4-methoxy)-phenyl (5-chloro)-2-thienyl ketone (m.p. = 162° C after recrystallisation from toluene).

The mixture of amine hydrochlorides composed of 55% of the geometric isomer in the cis configuration in relation to thiophene and 45% of the cis isomer melts at 155° C after recrystallisation from ethyl acetate.

EXAMPLE 11

(2,3-Dichloro-4-methoxy)-phenyl 3-thienyl O-(diethylaminoethyl)-ketone oxime

Applying the method described in Example 1, 8 g of a mixture of the two geometric isomers of the desired oxime were obtained from 8.6 g of (2,3-dichloro-4-methoxy)-phenyl 3-thienyl ketone (m.p. = 140° C after recrystallisation from isopropanol) and 7.2 g of O-(diethylaminomethyl)-hydroxylamine dihydrochloride.

The mixture of amine hydrochlorides composed of 80% of the geometric isomer of the oxime in the trans configuration in relation to thiophene and 20% of the cis isomer melts at 177° C after recrystallisation from isopropanol.

EXAMPLE 12

Phenyl 2-furyl O-(diethylaminoethyl)-ketone oxime

Applying the method described in Example 1, this ether oxime was obtained in 40% yield.

The amine hydrochloride of the geometric isomer of the oxime which has the cis configuration in relation to the heterocyclic groups melts at 159° after recrystallisation from dioxane.

EXAMPLE 13

(2-Chloro-4-methoxy)-phenyl 2-furyl O-(diethylaminoethyl)-ketone oxime

Applying the method described in Example 1, 14 g of a mixture of the two geometric isomers of the desired oxime were obtained from 14 g of (2-chloro-4-methoxy)-phenyl 2-furyl ketone and 12.3 g of O-(diethylaminoethyl-hydroxylamine dihydrochloride.

The amine hemifumarate was prepared in ethanol by the action of fumaric acid on the oxime ether in stoichiometric proportions.

The mixture of hemifumarates consisting of 10% of the isomer in the cis configuration in relation to furane and 90% of the trans isomer melts at 120° C.

EXAMPLE 14

(3-Chloro-4-methoxy)-phenyl 2-furyl O-(diethylaminoethyl)-ketone oxime

Applying the method described in Example 1, a mixture of the two geometric isomers of the oxime ether was obtained in 50% yield.

The amine hydrochloride of the isomer in the cis configuration in relation to furane melts at 194° C after recrystallisation from isopropanol.

EXAMPLE 15

(2,3-Dichloro-4-methoxy)-phenyl-2-furyl O-(diethylaminoethyl)-ketone oxime

A. (2,3-Dichloro-4-methoxy)-phenyl 2-furyl ketone 40 g of anhydrous aluminium chloride were added little by little to a solution of 53.2 g of 2,3-dichloroanisole and 39.2 g of 2-furane-carboxylic acid chloride in 150 ml of methylene chloride which was kept at a temperature of 5° C. When all the aluminium chlorides had been added, the reaction mixture was left to return to room temperature and after stirring for 2 hours it was poured on 2 volumes of crushed ice and 20 ml of concentrated hydrochloric acid. When the mixture had returned to room temperature, the organic phase was decanted and the aqueous phase was extracted with methylene chloride. The two organic phases were combined, washed with a 2N aqueous soda solution and dried over sodium sulphate and the solvent was evaporated under reduced pressure. The residue was recrystallised from ethanol at 95% or from 1,2-dichloroethane. The ketone melting at 151° C was obtained in 75% yield.

B. (2,3-Dichloro-4-methoxy)-phenyl 2-furyl-ketone oxime

A solution of 20.4 g of (2,3-dichloro-4-methoxy)-phenyl 2-furylketone and 6 g of hydroxylamine hydrochloride in 75 ml of pyridine was kept at 110° C for 3 hours. The solvent was then evaporated under reduced pressure, water was poured over the residue and the precipitate was then isolated. This precipitate contained 70% of oxime. The unreacted ketone is removed by recrystallisation from chloroform. The mixture of the two isomers of this oxime, containing 40% of the isomer with the trans configuration in relation to furane and 60% of the cis isomer, melts at about 180° C.

C. (2,3-Dichloro-4-methoxy)-phenyl 2-furyl O-(diethylaminoethyl) ketone oxime A mixture of 7.15 g of the oxime previously obtained, 4.3 g of (2-chloro)-ethyl-diethylamine hydrochloride and 10.7 g of potassium carbonate in 50 ml of benzene was kept at 80° C for 10 hours. The precipitate was then isolated at room temperature, the benzene phase was washed with water and dried and the solvent was evaporated under reduced pressure. The residue was dissolved in ethyl ether. Gaseous hydrochloric acid was added until formation of a white precipitate was completed. This precipitate consists of the two amine hydrochlorides of the geometric isomers of the oxime. 9 g were isolated by filtration, m.p. = 150° C.

The hydrochloride of the geometric isomer which has the trans configuration in relation to furane was practically insoluble in water and may thus be separated from its homologue. After recrystallisation from isopropanol it melted at 175° C (slow melting point in capillary tube: 186° C). The hydrochloride of the cis isomer melts at 146°–148° C after recrystallisation from ethanol.

The amine methane sulphonate of the isomer which has the trans configuration in relation to furane, prepared by reacting one equivalent of methane sulphonic acid with a solution of the oxime ether in ethanol and precipitated from this reaction medium by the addition of ethyl ether melts at 146° C. The amine glycollate of the isomer which has the trans configuration in relation to furane, prepared by reacting one equivalent of glycollic acid with the amine in solution in an alcohol, melts at 100° C after recrystallization from isopropanol.

When this oxime ether is prepared by the method described in Example 1 by the action of O-(diethylaminoethyl)-hydroxylamine on (2,3-dichloro-4-methoxy)-phenyl 2-furyl ketone, the yield obtained was 70%. Thus about 70% of the geometric isomer which has the trans configuration in relation to furane is formed for 30% of the cis isomer.

EXAMPLE 16

(2,3-Dichloro-4-methoxy)-phenyl 2-furyl O-(diethylaminoethyl)-ketone oxime from (2,3-dichloro-4-methoxy)-phenyl 2-furyl O-(aminoethyl) ketone oxime

A. (2,3-Dichloro-4-methoxy)-phenyl 2-furyl O-(aminoethyl)-ketone oxime 14.3 g of the mixture of isomers of (2,3-dichloro-4-methoxy)-phenyl 2-furyl-ketone oxime prepared as in Example 15 were added to a solution of sodium ethylate in ethanol obtained by the addition of 4.6 g of sodium to 150 ml of absolute ethanol, and the mixture was heated to 50° C for one hour. It was then cooled to 20° C and 20.5 g of 2-bromoethylamine hydrobromide were introduced into the reaction mixture with stirring. After 4 hours at this temperature, the precipitate formed was isolated, the solvent was removed under reduced pressure and 150 ml of water were poured over the remaining solid. The mixture was acidified by the addition of 5N hydrochloric acid and the aqueous phase was washed with ether and then made alkaline by the addition of sodium carbonate, and the end product was then extracted with ether in 60% yield.

The amine hydrochloride of the geometric isomer which has the cis configuration in relation to furane melts at 206° C. The mixture of amine hemifumarates consisting of 60% of the trans isomer in relation to furane and 40% of the cis isomer melts at 188° C.

B. 7 g of the oxime ether obtained by the method described above and 7 g of bromoethane in 20 ml of absolute ethanol were stirred for 48 hours. Ethyl ether containing anhydrous hydrochloric acid was then added and the precipitate was filtered. The precipitate was then suspended in water and made alkaline by the addition of sodium carbonate and the aqueous phase was extracted with ether. The ethereal phase was dried, anhydrous hydrochloric acid was added and the precipitate of hydrochlorides formed was isolated. The end product was isolated after repeated recrystallisations from isopropanol; yield 50%.

EXAMPLE 17

2,3-Dichloro-4-methoxy)-phenyl 2-furyl O-(dimethylaminoethyl)-ketone oxime

Applying the method described in Examples 1, this oxime ether was obtained in 50% yield.

The mixture of amine hydrochloride consisting of 25% of the geometric isomer of the oxime in the cis configuration in relation to furane and 75% of the trans isomer melts at 188° C.

EXAMPLE 18

(2,3-Dichloro-4-metoxy)-phenyl 2-furyl O-(dimethylaminopropyl)-ketone oxime

Applying the method described in Example 1, a mixture of the two isomers of the oxime was obtained in 70% yield.

The mixture of amine hydrochlorides consisting of 35% of the isomer in the cis configuration in relation to furane and 65% of the trans isomer melts at 146°–148° C.

EXAMPLE 19

(2,3-Dichloro-4-methoxy)-phenyl 2-furyl O-(1-pyrrolidinyl-ethyl)-ketone oxime

Applying the method described in Examples 1, 12 g of a mixture of the two isomers of this oxime were obtained from 13.55 g of (2,3-dichloro-4-methoxy)-phenyl 2-furyl ketone and 10.15 g of O-(1-pyrrolidinyl-ethyl)hydroxylamine dihydrochloride (m.p. = 150° C after recrystallisation from ethanol).

The mixture of amine hydrochlorides consisting of 30% of the geometric isomer of the oxime in the cis configuration in relation to the heterocyclic group and 70% of the trans isomer melts at 161° C.

EXAMPLE 20

(2,3-Dichloro-4-ethoxy)-phenyl 2-furyl O-(diethylaminoethyl)-ketone oxime

Applying the method described in Example 1, 17.9 g of the oxime ether were obtained from 14.25 g of (2,3-dichloro-4-ethoxy)-phenyl 2-furyl ketone (m.p. = 119° C after recrystallisation from methylene chloride) and 11.5 g of O-(diethylaminoethyl)-hydroxylamine dihydrochloride.

The mixture of amine hydrochlorides consisting of 10% of the geometric isomer in the cis configuration in relation to furane and 90% of the trans isomer melts at 131° C. The mixture of hydrochlorides consisting of 95% of the cis isomer in relation to the heterocyclic group and 5% of the trans isomer forms a solvate with isopropanol, the solvate having a melting point of 158° C.

EXAMPLE 21

(2,4-Dimethoxy)-phenyl 2-furyl O-(diethylaminoethyl)-ketone oxime

A - (2,4-Dimethoxy)-phenyl 2-furyl-ketone oxime

Prepared by the method described in Example 15(B) in 60% yield.

The mixture of the two geometric isomers of the oxime containing 40% of the isomer in the trans configuration in relation to furane and 60% of the cis isomer melts at 100° C.

B - (2,4-Dimethoxy)-phenyl 2-furyl O-(diethylaminoethyl) ketone oxime 1.2 g of a 50% suspension of sodium hydride in oil were slowly added to a solution of 6 g of the mixture of isomers of the above mentioned oxime in 30 ml of anhydrous dimethyl formamide, followed by 3.25 g of (2-chloro)-ethyl-diethylamine. After stirring for 2 hours the solution was poured into 250 ml of water and acidified by the addition of 5N hydrochloric acid. The aqueous phase was washed with ether and made alkaline by the addition of sodium carbonate and the end product was extracted with ether. The ethereal solution was dried, the solvent was evaporated, and 5 g of the oxime ether consisting of a mixture of the two geometric isomers were then isolated.

The mixture of amine hydrochlorides consisting of 45% of the geometric isomer of the oxime in the cis configuration in relation to furane and 55% of the trans isomer melts at 132° C.

EXAMPLE 22

(2,4-Dimethyl)-phenyl 2-furyl O-(diethylaminoethyl) ketone oxime

This compound was prepared by the method described in Example 1 from (2,4-dimethyl)-phenyl 2-furyl-ketone (b.p.$_{8\ mm\ Hg}$ = 158°-162° C); yield 50%.

The mixture of amine-hydrochlorides composed of 35% of the geometric isomer in the cis configuration in relation to furane and 65% of the trans isomer melts at 116° C.

EXAMPLE 23

(2,3-Dichloro-4-methoxy)-phenyl (5-bromo)-2-furyl O-(diethylaminoethyl)-ketone oxime This compound was prepared in 50% yield by the method described in Example 1 but using butanol-1 as solvent.

The amine hydrochloride of the geometric isomer which has the trans configuration in relation to furane melts at 201° C after recrystallisation from dioxane.

EXAMPLE 24

(2,3-Dichloro-4-methoxy)-phenyl 3-furyl O-(diethylaminoethyl)-ketone oxime

This compound was prepared by the method described in Example 1 from (2,3-dichloro-4-methoxy)-phenyl 3-furyl ketone (m.p. = 129°-130° C after recrystallisation from ethanol) and O-(diethylaminoethyl)-hydroxylamine dihydrochloride in 50% yield.

The mixture of amine hydrochlorides composed of 35% of the isomer in the cis configuration in relation to furane and 65% of the trans isomer melts at 135° C after recrystallisation from ethyl acetate.

EXAMPLE 25

(2,3-Dichloro-4-methoxy)-phenyl-(5-nitro)-2-thienyl O-(diethylaminoethyl) ketone oxime This compound was prepared by the method described in Example 1 from (5-nitro)-2-thienyl (2,3-dichloro-4-methoxy)-phenyl ketone (m.p. = 140° C).

The mixture of hydrochlorides composed of 75% of the cis isomer in relation to thiophene and 25% of the trans isomer melts at 180° C.

The compounds of the invention, in the form of their acid addition salts, have been the object of a toxicological and pharmacological study which has shown their therapeutic importance.

The two geometric isomers of the oxime ethers of formula I have similar pharmacological activities but with differing intensities.

The acute toxicity was determined on mice: The products dissolved in distilled water were injected intraveneously in amounts of 0.5 ml per 20 g of body weight into homogeneous batches of mice having an average weight of 20 g ± 2 g. The mortalities were determined at the end of 24 hours and the LD$_{50}$ values calculated by the statistical method of Bliss (Quart, J. Pharm. Pharmacol. 11, 192 (1938)). For all the compounds, the LD$_{50}$ was found to be situated between 10 and 40 mg/kg, that is to say comparable to that of papaverine hydrochloride (33 mg/kg under the same conditions) and slightly superior to that of dipyridamole.

These compounds have an antispasmodic activity which was demonstrated in vitro on an isolated organ. A loop of rad duodenum kept alive in an aerated bath of 50 ml of tyrode solution at a temperature of 38° C is contracted periodically by the addition of a solution of barium chloride. The products under investigation were added to the solution to determine the concentration required to produce 50% inhibition of the contractions. All the compounds showed an activity at least comparable to that of papaverine hydrochloride and some were even 10 to 20 times superior (see Table I below).

The coronary vasodilatory activity of the products according to the invention was studied in the dog anaesthatised by intravenous injection of mebubarbital. The following were recovered by means of a "BECKMAN Dynograph" polygraph: Cardiac rhythm, arterial pressure at the level of the carotid artery, variations in coronary vasomotor activity determined by an electromagnetic flow meter, and the variation with time of the elevation in pressure of the left endocavitory or intra-aortic blood medium. The following effects were demonstrated: Bradycardiac activity in all the compounds, the slowing down of cardiac rhythm being proportional to the dose injected;

Pronounced coronary vasodilatory activity which, taking into account the toxicity of the compounds is distinctly superior to that of papaverine hydrochloride and of dipyridamole (see Table II below), and an improvement in the efficiency of heart muscle contraction, which is translated into an increase in the rate of rise of intracardiac pressure after injection of the compounds of the invention.

TABLE I

| Compound of Example | 6 | 6 | 7 | 11 | 15 | 15 | 20 | 20 | 24 | Papaverine |
|---|---|---|---|---|---|---|---|---|---|---|
| Trans isomer in relation to the heterocyclic group (in %) | 60% | 0% | 90% | 80% | 100% | 0% | 5% | 90% | 65% | |
| C µg/ml | 0.71 | 1.42 | 0.14 | 0.36 | 0.35 | 3.60 | 3.60 | 0.28 | 0.56 | 5 |

TABLE II

| Compound of Example | 6 | 6 | 11 | 15 | 15 | 24 | Dipyridamole |
|---|---|---|---|---|---|---|---|
| Trans isomer in relation to the heterocyclic group (in %) | 60% | 0% | 80% | 100% | 0% | 65% | |
| Vasodilation after 1 mn | 0.71 | 0.92 | 1.93 | 1 | 1 | 1.35 | 0.37 |
| Vasodilation after 5 mn | 0.68 | 0 | 1.25 | 1 | 0.33 | 0.49 | 0.33 |
| Vasodilation after 15 mn | 0.32 | 0 | 2.35 | 1 | 0 | 0 | 0.55 |

We claim:
1. An aromatic compound having the formula:

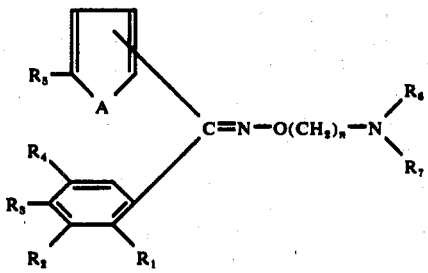

in which,
A in the heterocyclic group is selected from the group consisting of O and S;
$R_1$, $R_2$, $R_3$, and $R_4$, which may be identical or different, are selected from the group consisting of hydrogen, halogen, lower alkyl, lower alkoxy and lower alkoxylidene;
$R_5$ is selected from the group consisting of hydrogen, lower alkyl, and nitro;
n is an integer from 1 to 3; and
$R_6$ and $R_7$ which are identical or different lower alkyl groups;
and pharmaceutically acceptable acid addition salts of the amino group; said compound being in the form of the cis isomer, the trans isomer or mixtures thereof.

2. The compound according to claim 1 in which said oxime is the trans isomer.

3. The compound according to claim 1 in which said oxime is the cis isomer.

4. The compound according to claim 1 which is a mixture of the cis and trans isomers.

5. The compound of claim 1 which is selected from the group consisting of (2,3-dichloro-4-methoxy)-phenyl 2-thienyl O-(diethylaminoethyl) ketone oxime, the cis geometric isomer of said compound, the trans geometric isomer of said compound, and an acid addition salt of said compound or its geometric isomers.

6. The compound of claim 1 which is selected from the group consisting of (2,3-dichloro-4-methoxy)-phenyl 3-thienyl O-(diethylaminoethyl) ketone oxime, the cis geometric isomer of said compound, the trans geometric isomer of said compound, and an acid addition salt of said compound or its geometric isomers.

7. The compound of claim 1 which is selected from the group consisting of (2,3-dichloro-4-methoxy)-phenyl 2-furyl O-(diethyl-aminoethyl) ketone oxime, the cis geometric isomer of said compound, the trans geometric isomer of said compound, and an acid addition salt of said compound or its geometric isomers.

8. The compound of claim 1 which is selected from the group consisting of (2,3-dichloro-4-ethoxy)-phenyl 2-furyl O-(diethylaminoethyl) ketone oxime, the cis geometric isomer of said compound, the trans geometric isomer of said compound, and an acid addition salt of said compound or its geometric isomers.

9. The compound of claim 1 which is selected from the group consisting of (2,3-dichloro-4-methoxy)-phenyl 3-furyl O-(diethylaminoethyl) ketone oxime, the cis geometric isomer of said compound, the trans geometric isomer of said compound, and an acid addition salt of said compound or its geometric isomers.

10. A method of inducing coronary vasodilatory activity which comprises administering orally or parenterally to a host in need thereof a therapeutically effective amount of at least one compound according to claim 1.

11. A composition useful for inducing coronary vasodilatory activity which comprises a therapeutically effective amount of a compound according to claim 1 and a physiologically acceptable excipient therefor.

* * * * *